United States Patent
Elvin et al.

(10) Patent No.: US 7,045,280 B2
(45) Date of Patent: May 16, 2006

(54) ASSAY METHOD (75) Inventors: Paul Elvin, Macclesfield (GB); Philip Edwin Pinder, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 23 days.

(21) Appl. No.: 10/130,368

(22) PCT Filed: Dec. 5, 2000

(86) PCT No.: PCT/GB00/04647

§ 371 (c)(1),
(2), (4) Date: May 17, 2002

(87) PCT Pub. No.: WO01/42488

PCT Pub. Date: Jun. 14, 2001

(65) Prior Publication Data

US 2004/0211940 A1    Oct. 28, 2004

(30) Foreign Application Priority Data

Dec. 8, 1999    (GB) .................................. 9928882.1

(51) Int. Cl.
*C12Q 1/00* (2006.01)
*C12N 9/72* (2006.01)
*C07K 14/00* (2006.01)

(52) U.S. Cl. .......................... 435/4; 435/183; 435/215; 514/2; 530/350

(58) Field of Classification Search .................... 435/4, 435/183, 215; 514/2; 530/350
See application file for complete search history.

(56) References Cited

U.S. PATENT DOCUMENTS 4,910,190 A    3/1990    Bergeson et al. .............. 514/19
5,955,284 A    9/1999    Braxton et al. ................. 435/6

OTHER PUBLICATIONS

Sugimori et al. Inhibitory Properties of Recombinant Human Monocyte/Neutrophil Elastase Inhibitor (Sep. 1995) Am. J. Respir Cell Molec. Biol. vol. 13, pp. 314-322.*

Nicolini et al. Leukocyte elastase inhibition and t-PA-induced coronary artery thrombolysis in dogs: Beneficial effects on myocardial histology (Nov. 1991) vol. 122, No. 5, pp. 1245-1251.*

Gilboa et al. Evidence for Regulation of Endothelial Plasminogen-Activating System by Polymorphonuclear Leukocyte Elastase (1989) vol. 54, pp. 467-475.*

Mazar et al. The urokinase plasminogen activator system in cancer: Implications for tumor angiogenesis and metastasis (1999 Angiogenesis vol. 3, pp. 15-32.*

Bach-Gansmo et al., "Degradation of the a-Chain of Fibrin by Human Neutrophil Elastase Reduces the Stimulating Effect of Fibrin on Plasminogen Activation", Thrombosis Research, vol. 75, No. 3, pp. 307-317, 1994.

Banda et al, "The Role of Macrophage Elastase in the Proteolysis of Fibrinogen, Plasminogen, and Fibronectin", Federation Proceedings 39(6), Abstract 804.

Chung, et al., "Factors That Control Extravascular Fibrinolysis", Seminars in Thrombosis and Hemostasis, vol. 22, No. 6, pp. 479-488, 1996.

Dunbar, et al., "Cancer Treatment with Inhibitors of Urokinase-Type Plasminogen Activator and Plasmin", Ashley Publications Ltd. ISSN 1354-3784, pp. 2085-2092; 2000.

Gilboa, et al., "Neutrophil Elastase Modulates the Plasminogen Activating System of Cultured Rat Mesangial Cells", Clinical Research, vol. 40, No. 2, p. 319A, 1992.

Heiden et al., "The Role of Inflammatory Cells and Their Proteases in Extravascular Fibrinolysis", Seminars in Thrombosis and Hemostasis, vol. 22, No. 6, pp. 497-501, 1996.

Kanayama et al., "Inactivation of Human Tumor Cell Pro-urokinase by Granuloctye Elastase", Jpn J. Cancer Res. 81, 994-1002, Oct. 1990.

(Continued)

*Primary Examiner*—Nashaat T. Nashed
*Assistant Examiner*—Holly Schnizer
(74) *Attorney, Agent, or Firm*—Fish & Neave IP Group Ropes & Gray LLP (57) ABSTRACT

The present invention provides a method for the measurement of the activity of a plasminogen activator, such as urokinase plasminogen activator (uPA) or tissue plasminogen activator (tPA) in a biological sample using an assay method characterized by the inclusion of an elastase inhibitor in the assay mixture. The invention also provides a diagnostic kit for the measurement of a plasminogen activator using said method and a method of determining the effective therapeutic dose of a plasminogen activator inhibitor using said method. Also provided is a method of preparing a pharmaceutical composition.

4 Claims, 4 Drawing Sheets

OTHER PUBLICATIONS

Kikuchi, et al., "Adjuvant Effects of Tranexamic Acid to Chemotherapy in Ovarian Cancer Patients with Large Amount of Ascites", Acta Obstet Gynecol Scand, 65:453-456, 1996.

Lentschener, et al., "Intraoperatively-adminstered aprotinin and survival after elective liver resection for colorectal cancer metastasis—A preliminary study", Fibrinolysis & Proteolysis (1999) 13 (1), 39-45.

Machovich et al., "An Elastase-Dependent Pathway of Plasminogen Activation", Biochemistry 28, pp. 4517-4522, 1989.

Machovich et al., "The Elastase-Mediated Pathway of Fibrinolysis", Blood Coagualtion and Fibrinolysis, 1 pp. 79-90, 1990.

Nagamatsu et al., "Effects of Human Granulocyte Elastase on Fibrinolysis", Chem. Pharm. Bull. 29 (4) 1121-1129 (1981).

Serdengecti, et al., "Overal Survival Results of Non-Small Cell Lung Cancer Patients: Chemotherapy Alone Versus Chemotherapy with Combined Immunomodulation", Chemioterapia, vol. 7—n. 2 (122-126), 1998.

Simon et al., "Fibrin(ogen) is Internalized and Degraded by Activated Human Monocytoid Cells Via Mac-1 (CD11b/CD18): A Nonplasmin Fibrinolytic Pathway", Bood, vol. 82, No. 8, Oct. 15, 1993, pp. 2414-2422.

Simon et al, "The Fibrin(ogen)alytic Properties of Cathepsin D", Biochemistry 33, pp. 6555-6563, 1994.

Simon et al., "Mac-1 (CD11b/CD18) and the Urokinase Receptor (CD87) Form a Functional Unit on Monocytic Cells", Blood, vol. 88, No. 8, Oct. 15, 1996, pp. 3185-3194.

Soma, et al, "Treatment of Advanced Ovarian Cancer with Fibrinolytic Inhibitor (Tranexamic Acid)", Acta Obstet Gynecol Scand 59:285-287, 1980.

Toki et al., "Studies of the Activation Mechanism of Fibrinolytic Enzyme System in Plasma by Human Pancreatic Elastase", Thromb Haemostas (Stuttgart) 47 (1) 8-13 (1982).

Urano, et al., "Novel Mechanism to Enhance tPA-Induced Fibrinolysis: Effect of Limited Proteolysis of PAI-1 by Neutrophil Elastase", Polish Journal of Pharmacology, 48, pp. 209-213; 1996.

Vassalli et al., "Amiloride Selectively Inhibits the Urokinase-Type Plasminogen Activator", Federation of European Biochemical Societies, vol. 214, No. 1, 187-191, Apr. 1987.

Wojta et al., "Evaluation of Fibrinolytic Capacity in Plasma during Thrombolytic Therapy with Single (scu-PA) or Two-Chain Urokinase Type Plasminogen Activator (tcu-PA) by a Combined Assay System for Urokinase Type Plasminogen Activator Antigen and Function", Thrombosis and Haemostasis 61 (2) pp. 289-293, 1989.

Wu et al., "The Cleavage and Inactivation of Plasminogen Activator Inhibitor Type 1 by Neutrophil Elastase: The Evaluation of Its Physiologic Relevance in Fibrinolysis", Blood, Nol 86, No. 3, pp. 1056-1061, Aug. 1, 1995.

* cited by examiner

ASSAY METHOD

RELATED APPLICATIONS

This application is a national stage filing under 35 U.S.C. 371 of PCT application PCT/GB00/04647, filed Dec. 5, 2000, which claims priority from Great Britain Application No. 9928882.1, filed Dec. 8, 1999, the specifications of each of which are incorporated by reference herein.

This invention relates to the use of an elastase inhibitor in assays to determine the activity of plasminogen activators such as, urokinase plasminogen activator (uPA) or tissue plasminogen activator (tPA).

The metastatic behaviour of epithelial tumour cells is arguably the major factor contributing to patient survival and treatment failure. Metastasis is recognised as a complex dynamic process influenced by properties of both tumour cells and cellular compartments of normal tissues. The process is influenced by soluble mediators such as growth factors, cytokines, and hormones derived from both tumour and host cells, and through signalling via cell adhesion receptors both between cells and with the extracellular matrix. Metastatic dissemination of epithelial tumours to sites distant from the primary tumour proceeds by both vascular and lymphatic routes. Although epithelial tumours do not in themselves possess lymphatic vessels, once tumour cells have gained access to the local vasculature, vasolymphatic junctions ensure dissemination by both routes. Epithelial tumour cells may gain access to the capillaries and small venules by either tumour cell shedding as a result of mechanical pressure or by destruction of normal tissue structure as a result of invasive growth.

Normal epithelial cells are separated from underlying supporting tissue by a specialised extracellular matrix called basement membrane, composed of collagens and other proteins. The initial event distinguishing benign and invasive tumour growth is the destruction of the basement membrane and the subsequent penetration of tumour cells into underlying stroma. The invasive behaviour of tumour cells arises through alterations in cell adhesion, cell motility, and the ability of tumour cells to degrade components of the basement membrane. A number of proteolytic enzymes have been associated with tumour cell invasion including cathepsins, metalloproteases and plasminogen activators, all of which contribute to the destruction of the extracellular matrix.

Plasminogen activators convert the inactive zymogen plasminogen to the serine protease plasmin which can degrade a number of extracellular matrix proteins including fibronectin and laminin. Although plasmin itself does not degrade type IV collagen, a major component of basement membranes, the enzyme can activate the pro-enzyme forms of certain metalloproteases, such as gelatinase B, stromelysin and matrilysin, which are known to digest type IV collagen, a major component of basement membranes. In addition, Stromelysin may activate gelatinase A, another enzyme known to digest type IV collagen. Thus plasmin may be responsible for destruction of the extracellular matrix through direct enzyme activity, and as a result of activating a cascade of proteolytic enzymes.

There are two known plasminogen activators, urokinase or uPA, and tissue plasminogen activator or tPA. Both enzymes are present in plasma and play a critical role in fibrinolysis. Although tPA appears to be the key plasminogen activator in plasma, urokinase is associated with cell surface plasminogen activation as a result of binding to a specific cell surface urokinase receptor (uPAR, CD87). The uPAR plays a critical role in the regulation of cellular plasminogen activation; the single chain precursor form of uPA is activated more efficiently when receptor bound; the catalytic efficiency of receptor bound uPA is increased relative to uPA in solution phase; PAI-1 is less efficient as an inhibitor of receptor bound uPA. Since plasminogen is also cell surface bound the process of plasmin generation proceeds more effectively at the cell surface, and plasmin itself is less susceptible to inhibition when active at the cell surface. For a review of the urokinase system the reader is referred to: Andreasen et al (1997) International Journal of Cancer 72, 1–22.

Thus there is a medical need for antagonists of the uPA receptor or inhibitors of uPA, which are expected to inhibit the invasive behaviour of tumour cells. An essential tool for the identification and development of uPA receptor antagonists or uPA inhibitors is an in-vitro assay for the measurement of inhibition of uPA activity. Although cell surface uPA activity may be easily measured on the surface of cultured cell lines, there is a need to be able to demonstrate in vivo efficacy of receptor antagonists to enable pharmacodynamic measurements for dosing in man. However, the measurement of plasminogen activator activity in biological samples such as blood is difficult due to the co-existence of plasminogen activators, plasminogen activator inhibitors, and other protease activities in the blood, which may contribute to plasminogen-independent fibrinolysis and thus inaccurate measurements.

Plasminogen independent fibrinolysis may arise by a number of mechanisms including: potential for priming of the assay by virtue of cell surface plasminogen and plasmin associated with peripheral blood cells; activation of mononuclear cells due to the isolation procedure using ligation of a cell surface antigen; binding and internalisation of fibrinogen via the Mac-1 integrin, and subsequent intracellular fibrinolysis and activation of the mononuclear cells; activation of plasminogen by other proteases; and the potential for additional fibrinolytic enzymes to be released from the cells.

A number of enzymes including cathepsins and elastase may contribute to monocyte/macrophage fibrinolysis through cleavage of fibrinogen, or by activation of plasminogen.

Surprisingly we have found that the inclusion of an elastase inhibitor in an assay for the activity of a plasminogen activator, such as uPA or tPA, is sufficient to inhibit the plasminogen activator independent fibrinolysis, thus allowing accurate determination of plasminogen activator activity.

Thus according to the present invention there is provided a method for the measurement of the activity of a plasminogen activator in a biological sample using an assay method characterised by the inclusion of an elastase inhibitor in the assay mixture.

According to a further aspect of the invention there is provided the use of an elastase inhibitor in an assay mixture for the determination of the activity of a plasminogen activator in a biological sample.

According to a further aspect there is provided an assay method for the measurement of the activity of a plasminogen activator in a biological sample, comprising (a) mixing the biological sample with an assay mixture in the presence of an elastase inhibitor; and (b) measuring a signal which is proportional to the plasminogen activator activity in the cell sample.

According to a further aspect of the invention there is provided an assay method for the measurement of the activity of a plasminogen activator in a biological sample, comprising (a) mixing the biological sample with an assay mixture in the presence of an elastase inhibitor; and
(b) measuring the plasminogen activator activity in the biological sample.

The skilled man would appreciate that the biological sample may be purified or partially purified before inclusion in the assay. For example peripheral blood leukocytes may be purified from blood as described in example 2.

The assay mixture comprises reagents suitable for measuring plasminogen activator activity; such reagents are readily selectable by a person skilled in the art.

For example, a preferred assay mixture comprises a suitable buffer, a labelled substrate, which when cleaved yields a measurable signal, and optionally any other co-factors which may be required. This labelled substrate may be directly cleaved by the plasminogen activator or may cleaved by an intermediate element optionally contained in the assay mixture, such as another protein, which is itself activated by the plasminogen activator. The skilled man will appreciate that this intermediate element may consist of more than one component, the first of which is activated by the plasminogen activator and leads to a cascade of activation steps, culminating in the cleavage of the labelled substrate. For example, a plasminogen activator may act on plasminogen to yield plasmin and plasmin then cleaves a labelled fibrin substrate to yield a measurable signal.

According to a further aspect of the invention there is provided a diagnostic kit for the measurement of the activity of a plasminogen activator in a biological sample comprising reagents for preparing an assay mixture of the invention and instructions for use thereof.

According to a further aspect of the invention there is provided a diagnostic kit for the measurement of the activity of a plasminogen activator in a biological sample, and for use with a method of the invention, the diagnostic kit comprising reagents for preparing an assay mixture and instructions for use thereof.

According to a further aspect of the invention there is provided a method of determining the effective dose of an inhibitor of a plasminogen activator, which comprises:
(a) dosing one or more humans or other mammals with a range of plasminogen activator inhibitor concentrations, preferably one or more humans;
(b) isolating a biological sample from step (a), preferably a cell sample;
(c) measuring plasminogen activator activity according to the method of the invention; and
(d) calculating the effective dose of the inhibitor from the measured signal.

It would be clear to the skilled man that the an inhibitor of a plasminogen activator is an inhibitor of the activity of a plasminogen activator.

It would be clear to the skilled man that an inhibitor of the activity of a plasminogen activator, could either act directly on the plasminogen activator or could act downstream on a component of a biochemical cascade which leads to activation of the plasminogen activator. For example, one step in the activation of urokinase plasminogen activator (uPA) is the localisation of uPA at it receptor, the urokinase plasminogen activator receptor (uPAR). Thus, an antagonist of the interaction of uPA with uPAR would also be considered as an inhibitor of uPA.

For the avoidance of doubt effective dose means the effective therapeutic dose for the treatment of a disease wherein inhibition of the activity of a plasminogen activator would be of therapeutic benefit.

The skilled man would be able to calculate the effective therapeutic dose from the degree of inhibition of the activity of the plasminogen activator in the biological sample. Preferably the degree of inhibition would be greater than 50%, more preferably 70% or above, most preferably 90% or above.

According to a further aspect of the invention there is provided a method of determining the effective therapeutic dose of an inhibitor of the activity of a plasminogen activator which comprises:
(a) dosing one or more humans or other mammals with a range of plasminogen activator inhibitor concentrations, preferably one or more humans;
(b) isolating a biological sample from said humans or other mammals, preferably a cell sample;
(c) measuring plasminogen activator activity using a method of the invention; and
(d) calculating the effective therapeutic dose of the inhibitor from the measured activity.

According to a further aspect of the invention there is provided a method of preparing a pharmaceutical composition of a plasminogen activator inhibitor which comprises:
(a) determining the effective dose of the inhibitor according to the method of the invention; and
(b) preparing a unit dose of inhibitor comprising an amount of inhibitor within the effective dose range and a pharmaceutically acceptable excipient.

According to a further aspect of the invention there is provided a method of preparing a pharmaceutical composition which comprises:
(a) determining the effective therapeutic dose of an inhibitor of a plasminogen activator by a method of the invention, and
(b) mixing the inhibitor in an amount within the effective therapeutic dose range and a pharmaceutically acceptable excipient.

According to a further aspect of the invention there is provided a pharmaceutical composition prepared by the above method of preparing a pharmaceutical composition.

The skilled man will appreciate that this effective therapeutic dose may be formulated in one or more preparations to be delivered to the patient over a defined period of time. The skilled man will also appreciate that once the effective dose has been determined further pharmaceutical compositions can be prepared which will have been indirectly prepared by the above methods.

According to a further aspect of the invention there is provided a plasminogen activator assay solution comprising an elastase inhibitor.

It would be clear to the skilled man that an assay mixture and an assay solution are the same.

Plasminogen activators include, uPA or tPA, preferably uPA.

The activity of elastase could be inhibited using a number of approaches, for example using a chemical inhibitor which acts at the enzyme's active site or an allosteric site on the enzyme, or alternatively using an antibody which binds to the enzyme and inhibits the activity. A number of elastase inhibitors have been described (for a review of elastase inhibitors see: Bernstein et al [1994] Progress in Medicinal Chemistry 31, 59–120). The skilled man would be able to select a suitable elastase inhibitor for use in an assay of the invention. Such an elastase inhibitor would not substantially inhibit the plasminogen activator being determined or substantially interfere with any other component of the assay. Compounds which are not specific elastase inhibitors but have elastase inhibitory activity as a component of their pharmacology may also be used, provided said inhibitors do not substantially inhibit the plasminogen activator, plasmin or interfere with another component of the assay. By substantially we mean less than 10% inhibition, preferably less than 5% inhibition.

Examples of substituted peptide derivatives which are elastase inhibitors can be found in European Patent, EP189305. An example of an elastase inhibitor from this patent is 3S-[4-[(4-bromophenyl)sulfonylaminocarbonyl] phenylcarbonyl]-L-valyl-N-[3-(1,1,1-trifluoro-4-methyl-2-oxopentyl)]-L-prolinamide, which is a particularly preferred inhibitor. This inhibitor may be used in a range of 10–100 µM. Preferably 20 µM.

It would be clear to the skilled man that the concentration of the elastase inhibitor in the assay would be dependent on the potency of the inhibitor. Preferably a concentration of at least twice the $IC_{50}$ of the inhibitor for the elastase enzyme is used.

During the isolation of a cell sample, activation of the cells may occur which may contribute to enhanced plasminogen independent fibrinolysis. Thus a more accurate measurement of plasminogen activator activity may be obtained if the elastase inhibitor is present during the isolation of the biological sample in addition to in the assay mixture.

The skilled man would appreciate that the term 'plasminogen independent fibrinolysis' used in this specification also refers to plasminogen independent cleavage of any substrate, such as labelled-fibrin, used to measure plasminogen activator activity A biological sample is a sample of animal material which includes, but not limited to, blood, urine, tissue sections, and tissue biopsies, preferably tissue biopsies or blood, most preferably blood. Tissue biopsies may be assayed as sections or may be assayed as a cell suspension.

Biological samples may be derived from a variety of animal species, preferably mammals, more preferably human, monkey, dog, guinea pig, rat or mouse, further preferably rat, mouse or human, most preferably human.

Plasminogen activator activity may be assayed using a wide variety of technologies, for example, fluorimetric assays, chromogenic assays, radiolabelled assays or chemiluminescence assays, preferably fluorimetric assays or chromogenic assays, most preferably fluorimetric assays.

For guidance for the design of biological assays the skilled man will be aware of a number of standard works. Examples of such standard works include: Knight (1995) Fluorimetric Assays of Proteolytic Enzymes, Methods in Enzymology 248, 18–34; and Chard (1978) An Introduction to Radioimmunoassay and related techniques, Elsevier/North-Holland Biomedical Press The invention will now be illustrated with reference to the following non-limiting examples and accompanying table and figures, wherein.

Table 1 shows the determination of cell associated uPA activity associated with human or rat peripheral blood leukocytes (PBL), as described in Example 4.

The following assay can be used to determine cell-surface associated urokinase activity. The assay is also applicable to isolated enzymes, and cell-surface associated uPA or tPA in cultured cell lines and freshly isolated peripheral blood cells. In these examples the elastase inhibitor is: 3S-[4-[(4-bromophenyl)sulfonylaminocarbonyl]phenylcarbonyl]-L-valyl-N-[3-(1,1,1-trifluoro-4-methyl-2-oxopentyl)]-L-prolinamide.

EXAMPLE 1

Preparation of Fibrinogen FITC

Fibrinogen FITC was prepared as described by Wu and Diamond (Analytical Biochemistry 224 83–91 1995). Briefly, 10 mg/ml fibrinogen was combined with 1 mg/ml FITC (fluorescein isothiocyanate) in 0.1M sodium bicarbonate buffer pH 9.0 and incubated at room temperature for 1 hour with stirring in the dark. The reaction was stopped by adding an equal volume of 0.3M hydroxylamine in bicarbonate buffer. Any precipitate that formed at this stage was re-dissolved by increasing the pH. The reaction was then dialysed for 12–16 hours against 50 mM tris HCl, 0.1M NaCl pH=7.4 with several changes of buffer. The concentration of fibrinogen-FITC was estimated from OD280 nm (a 1% solution of fibrinogen having an absorbance of 15.1). Aliquots (50 µl) of fibrinogen-FITC were stored at −80° C. until required (generally as prepared by this method the concentration of fibrinogen-FITC is in the micromolar range).

EXAMPLE 2

Isolation of Peripheral Blood Leukocytes from Blood

Peripheral blood leukocytes were isolated from blood using either antibody-coated magnetic beads (e.g. Dynal beads—superparamagnetic monodisperse polymer particles) or using density gradient centrifugation.

(a) Isolation of Peripheral Blood Leukocytes from Blood Using Antibody-coated Magnetic Beads Human blood (10 ml), was collected into a 1/10 volume of 3.8% tri-sodium citrate containing 20 µM (final concentration) elastase inhibitor. Peripheral blood mononuclear cells were isolated using Dynal beads coated with an anti-CD14 monoclonal antibody (Cat. M-450 CD14, Dynal UK). Briefly, human blood was incubated with Dynal anti-CD14 beads (volumes of blood sample and beads as per manufacturers recommendations) for 20 minutes at 4° C. Mononuclear cells were recovered by centrifugation and washed with two volumes of assay buffer (50 mM tris HCl, 0.1M NaCl, 0.1% BSA pH—7.4 containing 20 µM elastase inhibitor), counted using a Coulter Counter and adjusted to $10^6$–$10^7$ cells per ml in assay buffer as required.

(b) Isolation of Peripheral Blood Leukocytes from Blood Using Gradient Centrifugation.

Human blood (10 ml), was collected into a 1/10 volume of 3.8% tri-sodium citrate containing 20 µM (final concentration) elastase inhibitor. The anti-coagulated blood was layered onto the surface of 15 ml Polymorphprep density gradient media (Nycomed Pharma AS, cat 1001971) and the leukocytes separated by centrifugation at 2000 rpm for 30–35 minutes at 20° C. Following recovery of leukocytes from the gradient solution, trace red blood cell contamination was removed by hypotonic lysis by resuspension in 5 ml 150 mM ammonium chloride, 10 mM sodium bicarbonate, 0.1 mM EDTA. After 5 minutes, 45 ml HBSS was added to the cell suspension and the leukocytes recovered by centrifugation at 1200 rpm for 5 minutes at 20° C. The cells were resuspended in assay buffer containing the elastase inhibitor (20 µM), counted using a Coulter Counter and adjusted to $10^6$–$10^7$ cells per ml in assay buffer as required.

EXAMPLE 3

Demonstration that the Elastase Inhibitor does not Inhibit uPA, tPA or Plasmin

The elastase inhibitor 3S-[4-[(4-bromophenyl)sulfonylaminocarbonyl]phenylcarbonyl]-L-valyl-N-[3-(1,1,1-trifluoro-4-methyl-2-oxopentyl)]-L-prolinamide did not inhibit uPA, tPA, or plasmin activity as measured by chromogenic substrate assays using the specific uPA substrate S2444 (Quadratech) or the specific plasmin substrate S2251 (Quadratech) substrates respectively. Briefly, uPA (high molecular weight uPA Calbiochem, Cat. 627081), tpA (Quadratech, Cat. 821157) or plasmin (Quadratech, Cat. 810655) were diluted-in buffer comprising 0.5M tris HCl, 0.1% tween 20 pH 8.3. Urokinase activity was measured in a final volume of 100 µl containing 0.4 mM S2444 in assay buffer by following the increase in absorbance at 405 nm. The activity of tPA was measured in a final volume of 100 µl, containing 230 nM Spectrozyrne tPA substrate (American Diagnostica, Cat. 444L) and 40 µg per ml tPA stimulator (fibrin, Quadratech, Cat. 821116) and following the increase in absorbance at 405 nm. Plasmin activity was measured in a final volume of 100 µl containing 0.66 mM S2251, and following the increase in absorbance at 405 nm. The elastase inhibitor did not significantly inhibit the activity of uPA, tPA or plasmin; results in the table below refer to % inhibition at 100 µM elastase inhibitor.

| Enzyme | % inhibition |
| --- | --- |
| uPA (5 nM) | 2 |
| tPA (30 nM) | 9 |
| Plasmin (2.5 µg ml-1) | 2 |

EXAMPLE 4

Assay Method

Reaction conditions to determine plasminogen activator activity in solution by following plasminogen dependent fibrinolysis were modified from those described by Wu and Diamond (Analytical Biochemistry 224 83–91 1995) and carried out in Dynatech Microfluor B flat bottom 96 well plates (Dynex Technologies, Cat. 7805). Binding of labelled fibrinogen to the plates was blocked by incubating the plates prior to use with 300 µl per well 1% BSA.

Excess BSA solution was removed, and measurement of uPA or tPA activity was carried out in a final volume of 200 µl by adding to the wells 100 µl of cell suspension in assay buffer (50 mM tris HCl, 0.1M NaCl pH=7.4 containing 20 µM elastase inhibitor), followed by 100 µl substrate mix in assay buffer containing 1 µM plasminogen (Quadratech, Cat. 810633) and 200 nM fibrinogen-FITC. Plasminogen dependent fibrinolysis was measured by following the increase in fluorescence over 50 minutes in a Cytofluor plate reader at 37° C. (excitation 485 nm, emission 530 nm, gain 70). Control wells without plasminogen and buffer blanks were used to calculate plasminogen dependent fluorescence units for uPA (high molecular weight uPA Calbiochem, Cat. 627081) or tPA (Quadratech, Cat. 821157) standards. Typically, a concentration range of 0.3–5 µM plasminogen activator was used.

Figure 3:
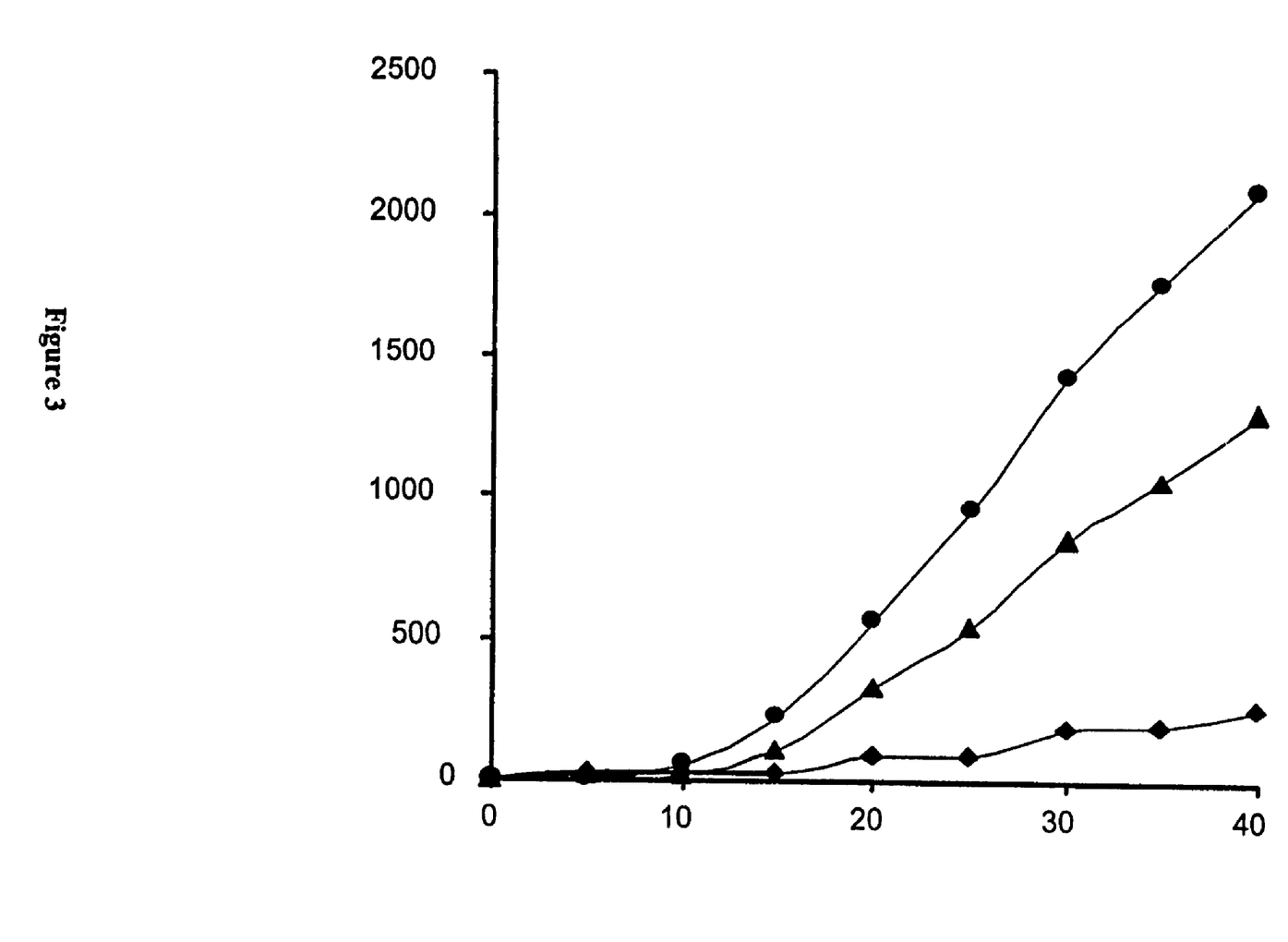
FIG. 3 shows plasminogen dependent fibrinolytic activity of human peripheral blood leukocytes in the presence of the elastase inhibitor together with tPA neutralising monoclonal antibody and amiloride, as described in Example 4. The X axis shows time measured in minutes and the Y axis shows fluorescence units. The solid circles depict leukocytes alone, the solid triangles depict leukocytes in the presence of amiloride and the solid diamonds depict leukocytes in the presence of a tPA neutralising monoclonal antibody and amiloride. The elastase inhibitor was present in each of the 3 conditions.

The dependence of the increase in fluorescence on plasminogen activator activity was demonstrated by the inclusion of specific inhibitors for either uPA or tPA (see FIG. 3). Inhibitors used were for uPA (amiloride, final concentration 100 µM or a neutralising anti-human uPA monoclonal antibody, e.g. Chemicon International Cat. 1336, final concentration 5 nM) and for tPA (a neutralising anti-human tPA: any active site directed neutralising antibody may be used e.g. American Diagnostica, Cat. ESP2, final concentration 30 nM).

Figure 1:
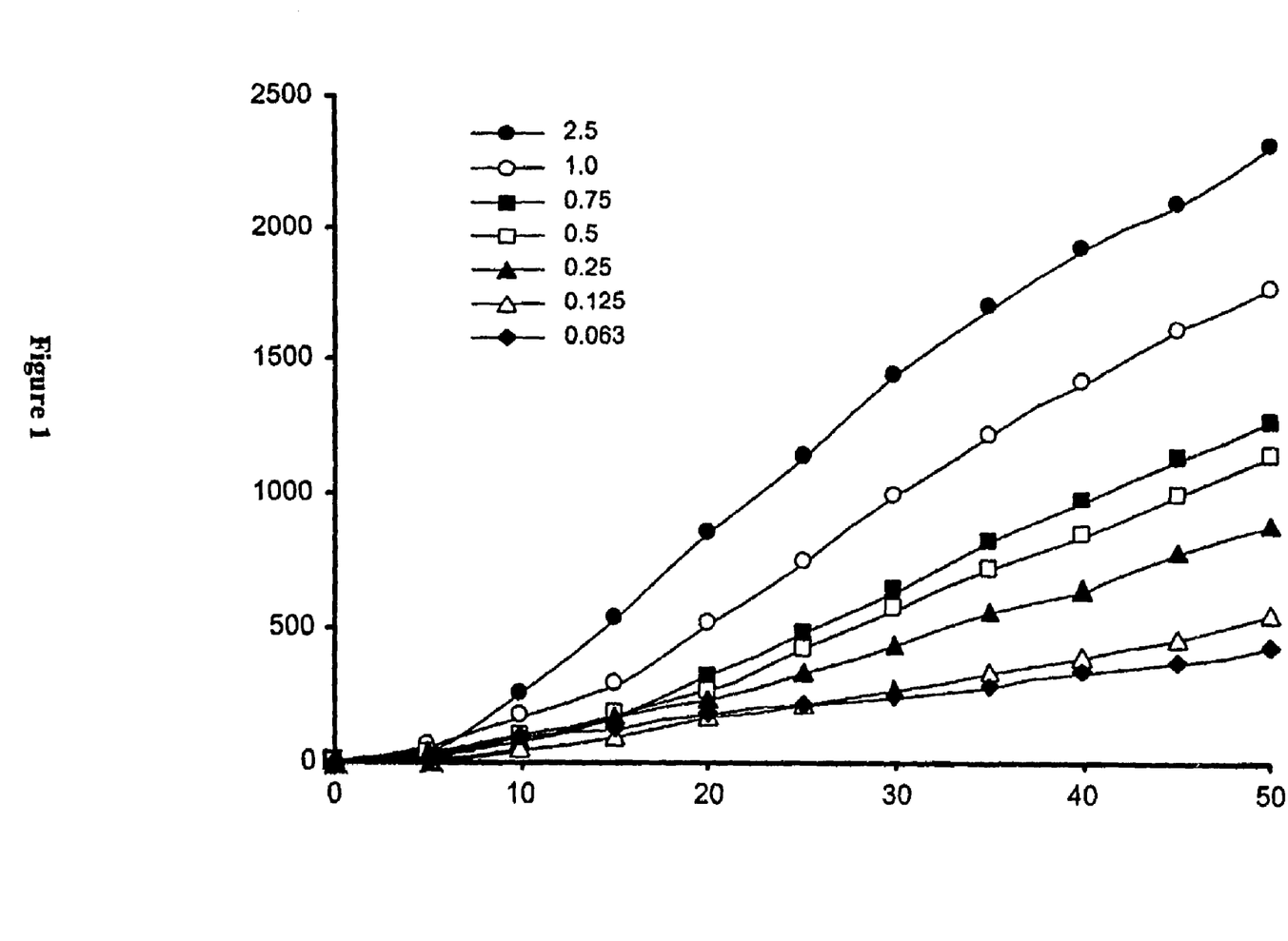
FIG. 1 shows the increase in fluorescence with time for a series of concentrations of uPA standards in solution, as described in Example 1. The X axis shows time in minutes, the Y axis shows fluorescence units and the legend shows the concentrations in picomoles of the uPA standards.
Figure 4:
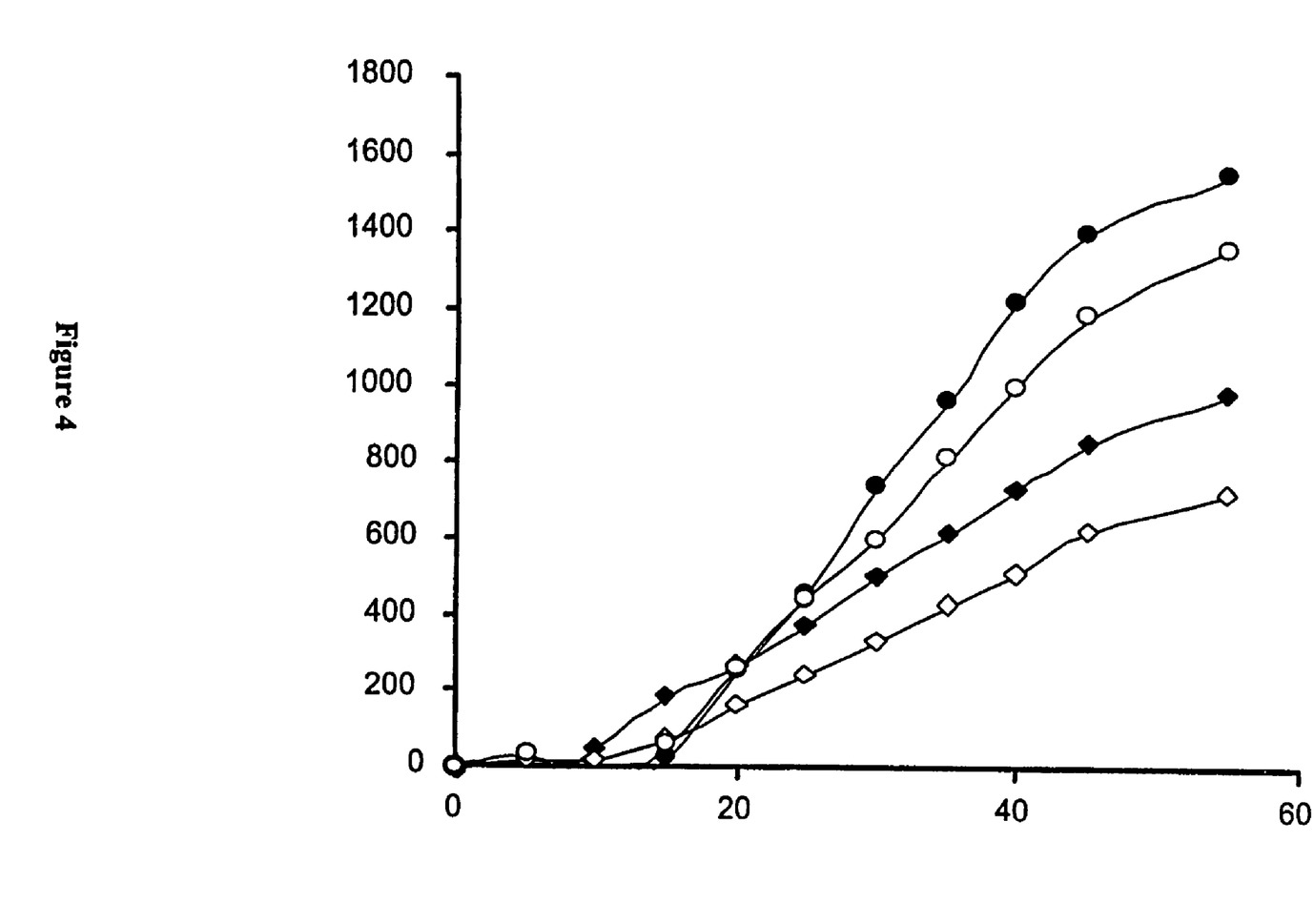
FIG. 4 shows the determination of uPA activity in peripheral blood leukocytes, as described in Example 4. The X axis shows time measured in minutes and the Y axis shows fluorescence units. The circles represent polymorphonuclear leukocytes, wherein the open circles represent $5 \times 10^5$ cells and the solid circles represent $10^6$ cells, and the diamonds represent monocytes, wherein the open circles represent $5 \times 10^5$ cells and the solid circles represent $10^6$ cells.

Urokinase plasminogen activator activity associated with peripheral blood leukocytes was estimated by comparison with the uPA standards (see FIG. 1). Alternatively, uPA activity may be estimated by determining the rate of change in fluorescence over the linear phase (20–40 minutes) of the fibrinolytic reaction. FIG. 4 shows the determination of uPA activity in peripheral blood leukocytes, in the presence of a tPA neutralising antibody.

This assay may be used in other animal species to measure plasminogen activator activity. For example Table 1 shows the measurement of cell associated uPA activity in a number of human and rat subjects.

EXAMPLE 5

Dose Response of the Inhibition of Plasminogen Activator Independent Fibrinolysis by the Elastase Inhibitor.

Figure 2:
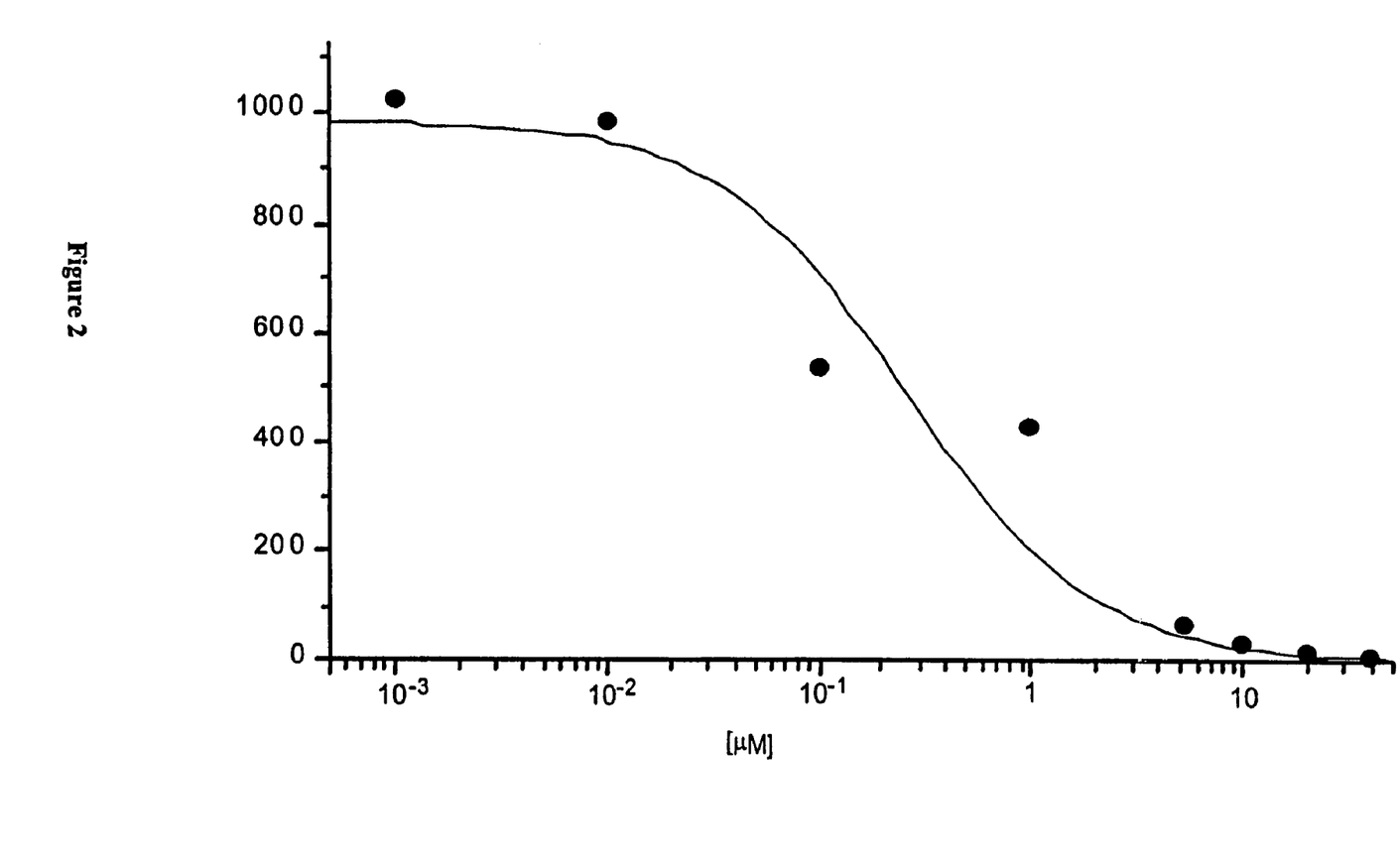
FIG. 2 shows a dose response curve for the inhibition of the plasminogen independent fibrinolysis by the elastase inhibitor, 3S-[4-[(4-bromophenyl)sulfonylaminocarbonyl] phenylcarbonyl]-L-valyl-N-[3-(1,1,1-trifluoro-4-methyl-2-oxopentyl)]-L-prolinamide, as described in Example 5. The Y axis shows the concentration of the elastase inhibitor in micromoles (µM) plotted on a logarithmic scale and the Y axis shows fluorescence units.

Peripheral blood leukocytes were prepared as described in Example 2 and diluted to $10^7$ cells per ml in assay buffer in the absence of the elastase inhibitor. Fibrinolysis was determined in the absence of plasminogen as described in Example 4; the assay wells included neutralising antibodies to uPA and tPA, and the elastase inhibitor at the concentrations indicated in the figure (0.001–40 mM). The data is shown in FIG. 2 and corresponds to fluorescence units after 45 minutes incubation time.

TABLE 1

Determination of cell associated uPA activity associated with human or rat peripheral blood leukocytes (PBL).

| Donor | pM uPA per $10^6$ cells |
|---|---|
| Human PBL | |
| D2664 | 0.51 |
| D5831 | 0.67 |
| D3244 | 0.30 |
| D7226 | 0.32 |
| D2502 | 0.26 |
| D9907 | 0.31 |
| mean ± SD | 0.40 ± 0.16 |
| Rat PBL | |
| 1 | 0.39 |
| 2 | 0.57 |
| 3 | 0.23 |
| 4 | 0.30 |
| 5 | 0.29 |
| 6 | 0.27 |
| 7 | 0.32 |
| 8 | 0.19 |
| 9 | 0.23 |
| 10 | 0.16 |
| mean ± SD | 0.29 ± 0.12 |

The invention claimed is:

1. An assay method for the measurement of the activity of urokinase plasminogen activator in a biological sample from a patient, comprising:
 (a) combining the biological sample from the patient with an assay mixture in the presence of an elastase inhibitor; and
 (b) measuring a signal which is proportional to the urokinase plasminogen activator activity in the biological sample,
 wherein the elastase inhibitor is 3S-[4-[(4-bromophenyl)sulfonylaminocarbonyl]phenylcarbonyl]-L-valyl-N-[3-(1,1,1-trifluoro-4-methyl-2-oxopentyl)]-L-prolinamide.

2. A method of determining the dose of an inhibitor of the activity of urokinase plasminogen activator effective to slow tumor progression which comprises:
 (a) dosing one or more humans or other mammals with a range of urokinase plasminogen activator inhibitor concentrations;
 (b) isolating a biological sample from said humans or other mammals;
 (c) measuring urokinase plasminogen activator activity using a method comprising:
  (i) mixing the biological sample with an assay mixture in the presence of an elastase inhibitor;
  (ii) measuring a signal which is proportional to the plasminogen activator activity in the cell sample; and
 (d) calculating the dose of the inhibitor of the activity of urokinase plasminogen activator effective to slow tumor progression from the measured activity.

3. A method of determining the dose of an inhibitor of the activity of urokinase plasminogen activator effective to slow tumor progression which comprises:
 (a) dosing one or more humans or other mammals with a range of urokinase plasminogen activator inhibitor concentrations;
 (b) isolating a biological sample from said humans or other mammals;
 (c) measuring urokinase plasminogen activator activity using a method comprising:
  (i) mixing the biological sample with an assay mixture in the presence of an elastase inhibitor, wherein the elastase inhibitor is a substituted peptide derivative;
  (ii) measuring a signal which is proportional to the plasminogen activator activity in the cell sample; and
 (d) calculating the dose of the inhibitor of the activity of urokinase plasminogen activator effective to slow tumor progression from the measured activity.

4. A method of determining the dose of an inhibitor of the activity of urokinase plasminogen activator effective to slow tumor progression which comprises:
 (a) dosing one or more humans or other mammals with a range of urokinase plasminogen activator inhibitor concentrations;
 (b) isolating a biological sample from said humans or other mammals;
 (c) measuring urokinase plasminogen activator activity using a method comprising:
  (i) mixing the biological sample with an assay mixture in the presence of an elastase inhibitor, wherein the elastase inhibitor is 3S-[4-[(4-bromophenyl)sulfonylaminocarbonyl]phenylcarbonyl]-L-valyl-N-[3-(1,1,1-trifluoro-4-methyl-2-oxopentyl)]-L-prolinamide;
  (ii) measuring a signal which is proportional to the plasminogen activator activity in the cell sample; and
 (d) calculating the effective therapeutic dose of the inhibitor of the activity of urokinase plasminopen activator from the measured activity.

* * * * *